| United States Patent [19] | [11] | 4,382,816 |
|---|---|---|
| Bahr | [45] | May 10, 1983 |

[54] HERBICIDAL TRITHIONE DERIVATIVES OF BENZOIC ACID

[75] Inventor: James T. Bahr, Hopewell, N.J.

[73] Assignee: Rhone-Poulenc Agrochimie, Lyons, France

[21] Appl. No.: 287,442

[22] Filed: Jul. 27, 1981

[51] Int. Cl.³ .................... A01N 43/32; C07D 339/04
[52] U.S. Cl. ............................................ 71/90; 549/37
[58] Field of Search ............................... 549/37; 71/90

[56] References Cited

U.S. PATENT DOCUMENTS

| 3,322,525 | 5/1967 | Martin et al. | 71/2.3 |
| 3,712,908 | 1/1973 | Bader et al. | 549/37 |
| 3,784,635 | 1/1974 | Theissen | 71/98 X |
| 3,983,168 | 9/1976 | Theissen | 260/501.16 |
| 3,994,923 | 11/1976 | Dingwall et al. | 549/37 |
| 4,063,929 | 12/1977 | Bayer et al. | 71/115 |
| 4,070,178 | 1/1978 | Johnson et al. | 71/105 |
| 4,285,723 | 8/1981 | Cartwright et al. | 71/103 |

FOREIGN PATENT DOCUMENTS 20052 12/1980 European Pat. Off. .
49-62637 6/1974 Japan .

*Primary Examiner*—Richard Raymond
*Attorney, Agent, or Firm*—Morgan, Finnegan, Pine, Foley & Lee

[57] ABSTRACT

There are provided herbicidal trithione derivatives of benzoic acids.

5 Claims, No Drawings

HERBICIDAL TRITHIONE DERIVATIVES OF BENZOIC ACID

BACKGROUND OF THE INVENTION

Herbicidal 5-[2-chloro-4-(trifluoromethyl)phenoxy]-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. Patents which describe such compounds and the like include U.S. Pat. Nos. 3,652,645; 3,784,635; 3,873,302; 3,983,168; 3,907,866; 3,798,276; 3,928,416; and 4,063,929.

SUMMARY OF THE INVENTION

This invention provides certain herbicidal compounds of the formula:

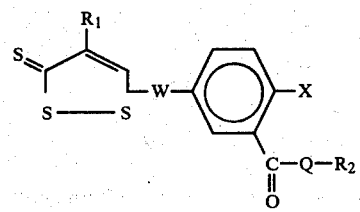

where:
(i) W is O or S;
(ii) Q is selected from the group consisting of O, S, and $NR_3$; and
(iii) X, $R_1$, $R_2$ and $R_3$ are groups which are capable of being incorporated into formula I and which collectively impart herbicidal activity thereto.

With respect to compounds of formula I which are capable of forming salts (e.g. where $QR_2$ is OH or $NHSO_2CH_3$), the invention also provides agronomically acceptable salts (e.g., alkali metal salts such as sodium salts or ammonium salts of the formula ($C_1$–$C_6$ alkyl)$_n$$NH_{4-n}$ where n is 0–4) of compounds of formula I.

Examples of the group X include halogen (e.g., F, Cl and Br), polyhaloalkyl (e.g., $C_1$–$C_4$ alkyl with from 2–9 halogens such as, especially, $CF_3$), $NO_2$, CN, alkyl (e.g., $C_1$–$C_4$ alkyl), $SO_2$ alkyl (e.g., having 1–4 carbon atoms), $SO_2NH_2$, NO, COO alkyl (e.g., having 2–5 carbon atoms) and COOH.

Examples of the groups $R_1$, $R_2$ and $R_3$ are as follows:
$R_1$ may be H or substituted or unsubstituted hydrocarbyl (e.g., having from 1 to 12 carbon atoms such as substituted or unsubstituted $C_1$–$C_{12}$ alkyl and substituted or unsubstituted $C_1$–$C_{12}$ aryl);
$R_2$ may be selected from the group consisting of H, substituted or unsubstituted hydrocarbyl (e.g., having from 1 to 12 carbon atoms such as substituted or unsubstituted $C_1$–$C_{12}$ alkyl and substituted or unsubstituted $C_1$–$C_{12}$ aryl) and, when Q is $NR_3$, electron withdrawing groups such as $SO_2$ alkyl $C_1$–$C_4$; and
$R_3$ is selected from the group consisting of H, substituted or unsubstituted hydrocarbyl (e.g., having from 1 to 12 carbon atoms such as substituted or unsubstituted $C_1$–$C_{12}$ alkyl and substituted or unsubstituted aryl) and, particularly when $R_2$ is an electron withdrawing group, $R_3$ may be groups such as Cl, CN, $CO_2$ alkyl ($C_2$–$C_5$), $SCCl_3$, etc.

Particular examples of the moiety $QR_2$ of formula I include OH, $OCH_2COOC_2H_5$, $OCH_2COOCH_3$, $OCH(CH_3)COOCH_3$, $OCH(CH_3)COOC_2H_5$ and $NHSO_2CH_3$. A particular example of the group $R_1$ is $CH_3$.

A preferred form of formula I is represented by the formula:

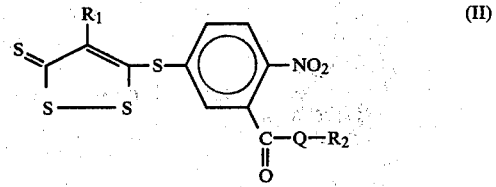

Preferred compounds according to the present invention are:

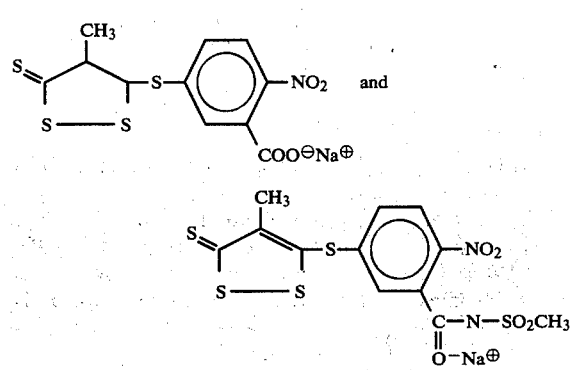

Compounds of formula I may be prepared by reaction of

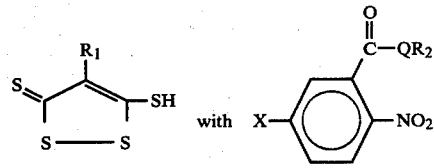

where X is F or Cl, under mildly basic conditions.

The compounds of this invention can be applied in various ways to achieve herbicidal action. They can be applied per se, but may be applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice, herbicidal application is measured in terms of pounds of herbicide applied per acre. The compounds of this invention are effective herbicides when applied in herbicidal amounts, e.g., at rates between about 0.03 pound and about 10 pounds per acre.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal compound and the salts thereof, having the following formula:

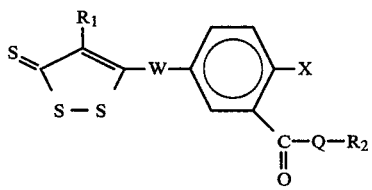

where:
(i) W is O or S;
(ii) Q is selected from the group consisting of O, S, and $NR_3$; and;
(iii) X is halogen, polyhaloalkyl, $NO_2$, CN, alkyl, $SO_2$ alkyl, $SO_2NH_2$, NO, COO alkyl and COOH;
(iv) $R_1$ is H or a hydrocarbyl of 1 to 12 carbon atoms;
(v) $R_2$ is selected from the group consisting of H, hydrocarbyl of 1 to 12 carbons, and, when Q is $NR_3$, $SO_2$ alkyl $C_1$ to $C_4$; and
(vi) $R_3$ is selected from the group consisting of H, hydrocarbyl of 1 to 12 carbon atoms and when $R_2$ is $SO_2$ alkyl $C_1$ to $C_4$, $R_3$ is selected from the group consisting of Cl, CN, $CO_2$ alkyl $C_1$ to $C_5$ and $SCCl_3$.

2. A herbicidal compound of the formula:

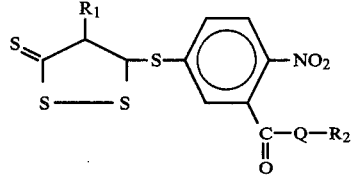

where $R_1$ is $CH_3$ and the moiety $QR_2$ is selected from the group consisting of OH, $OCH_2$, $COOC_2H_5$, $OCH_2COOCH_3$, $OCH(CH_3)COOCH_3$, $OCH(CH_3)$, $COOC_2H_5$ and $NHSO_2CH_3$.

3. A compound of the formula:

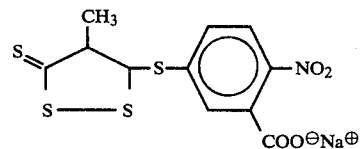

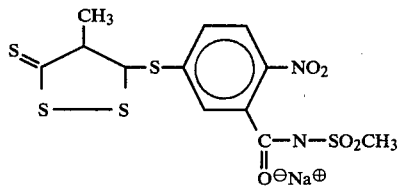

which is capable of herbicidal activity.

4. A herbicidal composition comprising an effective amount of a compound according to any one of claims 1 to 3 and an agronomically acceptable carrier.

5. A method for combating unwanted plants which comprises contacting them with a herbicidally effective amount of a compound according to any one of claims 1 to 3.

* * * * *